United States Patent [19]

Koros

[11] Patent Number: 5,384,336
[45] Date of Patent: Jan. 24, 1995

[54] BUBBLE COLUMN, TUBE SIDE SLURRY PROCESS AND APPARATUS

[75] Inventor: Robert M. Koros, Westfield, N.J.

[73] Assignee: Exxon Research & Engineering Co., Florham Park, N.J.

[21] Appl. No.: 159,407

[22] Filed: Nov. 30, 1993

Related U.S. Application Data

[63] Continuation-in-part of Ser. No. 956,188, Oct. 5, 1992, abandoned.

[51] Int. Cl.⁶ .......................... C07C 1/04; C07C 1/06
[52] U.S. Cl. .................................................. 518/700
[58] Field of Search ........................................ 518/700

[56] References Cited

U.S. PATENT DOCUMENTS

| | | |
|---|---|---|
| 2,287,092 | 6/1942 | Duftschmid et al. . |
| 2,853,369 | 9/1958 | Kolbel et al. . |
| 2,868,627 | 1/1959 | Kolbel et al. . |
| 4,751,057 | 6/1988 | Westerman . |
| 5,157,054 | 10/1992 | Herbolzheimer et al. . |

*Primary Examiner*—Howard T. Mars
*Attorney, Agent, or Firm*—Jay Simon

[57] ABSTRACT

A reactor housing having a plurality of reaction tubes vertically disposed therein for conducting slurry phase hydrocarbon synthesis reactions under substantially plug flow conditions, and wherein provision is made for uniformly distributing gas bubbles in slurry liquid into the reaction tubes.

7 Claims, 2 Drawing Sheets

BUBBLE COLUMN, TUBE SIDE SLURRY PROCESS AND APPARATUS

CROSS-REFERENCE TO RELATED APPLICATION

This application is a continuation-in-part of U.S. Ser. No. 956,188, filed Oct. 5, 1992.

FIELD OF THE INVENTION

This invention relates to a process and apparatus for conducting a substantially plug flow, slurry phase hydrocarbon synthesis (Fischer-Tropsch) process, wherein a slurried catalyst is dispersed in at least two, essentially parallel, reaction zones, e.g., reaction tubes, a common heat transfer medium surrounds each reaction zone, and gas bubbles in slurry liquid are uniformly distributed to each reaction zone.

BACKGROUND OF THE INVENTION

Slurry reactors are well known for carrying out highly exothermic, three phase, catalytic reactions. Usually called "bubble columns", these reactors have a liquid phase in which solid catalyst particles are dispersed or held in suspension by a gas phase bubbling through the liquid phase. These reactors provide improved heat transfer characteristics for the exothermic reaction, and the bubbling gas provides essentially all of the energy necessary for maintaining the catalyst dispersed in the liquid phase.

These bubble column reactors usually have a multiplicity of vertically arranged tubes suspended within a shell-type housing, the tubes being filled with a heat transfer medium, e.g., steam, which absorbs the heat generated by the exothermic reaction. Such reactors, however, operate at conditions that do not provide high productivity, that is, the rate per unit volume of slurry of CO and $H_2$ conversion to hydrocarbons, because of their relatively low length to diameter ratios.

Thus, there is a need for a slurry reactor which enhances the reaction rate of the gaseous reactants, efficiently dissipates heat, provides the desirable characteristics of plug flow, and allows for relatively easy replacement of catalyst in the event of declined activity, that is, the rate of conversion of synthesis gas ($H_2$+CO) to hydrocarbons is reduced.

SUMMARY OF THE INVENTION

In accordance with this invention, the Fischer-Tropsch hydrocarbon synthesis process is conducted in a multiplicity of slurry phase, bubble column type, vertically arranged reaction zones, each under substantially plug flow reaction conditions, and surrounded by a common fluid heat transfer medium. In some respects, the process can be described as being conducted in a shell and tube type reactor, longitudinally arranged about a vertical axis, not unlike a shell and tube heat exchanger, in which the reaction is effected on the tube side and the heat transfer medium is on the shell side.

The process is conducted in apparatus comprising:
a reactor housing, i.e., the shell;
more than one, and preferably a multiplicity, of essentially parallel, elongated, vertical reaction zones, i.e., tubes, disposed within the housing and within each zone a slurried catalyst is maintained;
inlet and outlet means for a heat transfer fluid, liquid or gas or mixture thereof, being in fluid communication and arranged such that the heat transfer fluid is in communication with the external surface of all or substantially all of the reaction zones; that is, the heat transfer fluid is free to flow through the housing between the upper and lower tube sheets and around every reaction tube;
gas inlet means adapted for receiving feed gas and uniformly dispersing gas bubbles into a liquid, e.g., slurry medium;
distribution means adapted for reducing bubble size or producing adequately small gas bubbles and uniformly distributing the gas bubbles to the reactor tubes;
slurry liquid inlet means;
outlet means for removing the liquid from the reactor housing; alternatively the apparatus can contain liquid product outlet means and separate slurry outlet means; outlet gas means for unconverted feed gas and product gas.

Consequently, as distinguished from the prior art where the process fluid is normally on the shell side of a shell and tube arrangement, the invention described herein maintains the process fluid on the tube side of a shell and tube reactor. Thus, because high length to diameter ratios can now be effected, the advantages for high productivity and high conversion can be obtained while still maintaining the slurry phase beneficial effects of excellent heat transfer and sufficient backmixing in the tubes to enhance selectivity to desired products.

BRIEF DESCRIPTION OF THE DRAWINGS

Turning to the drawings for a detailed description of the process and apparatus of this invention, items having the same numbers in different drawings refer to the same items.

FIG. 1 is a general layout of the invention where synthesis gas, i.e., hydrogen and carbon monoxide, in a ratio ranging from about 1 to 4, preferably, 1.5 to 2.75, more preferably about 1.7 to 2.5 is injected into the reactor housing 8 through conduit 12 at superficial gas velocities ranging from about 1 to 20 cm/sec, and through sparger 14 into liquid slurry medium, e.g., hydrocarbon synthesis wax, located in chamber 15. Thus, the gas is injected into an essentially catalyst free zone. The liquid level in the chamber 15 (shown by the wavy line) is maintained by a series of slotted tubes and bubble caps 19 located in distributor tray 18. Note that there is a gas space between distributor tray 18 and the liquid level in chamber 15. This gas space allows essentially even distribution of both gas and liquid into each tube. Without this gas "cushion", a perfectly mixed gas bubble/liquid mixture would be required in chamber 15 to ensure equal distribution to the reactor tubes, thereby requiring significant agitation. This apparatus/design virtually eliminates the need for such energy dissipation in chamber 15.

Figure 1:
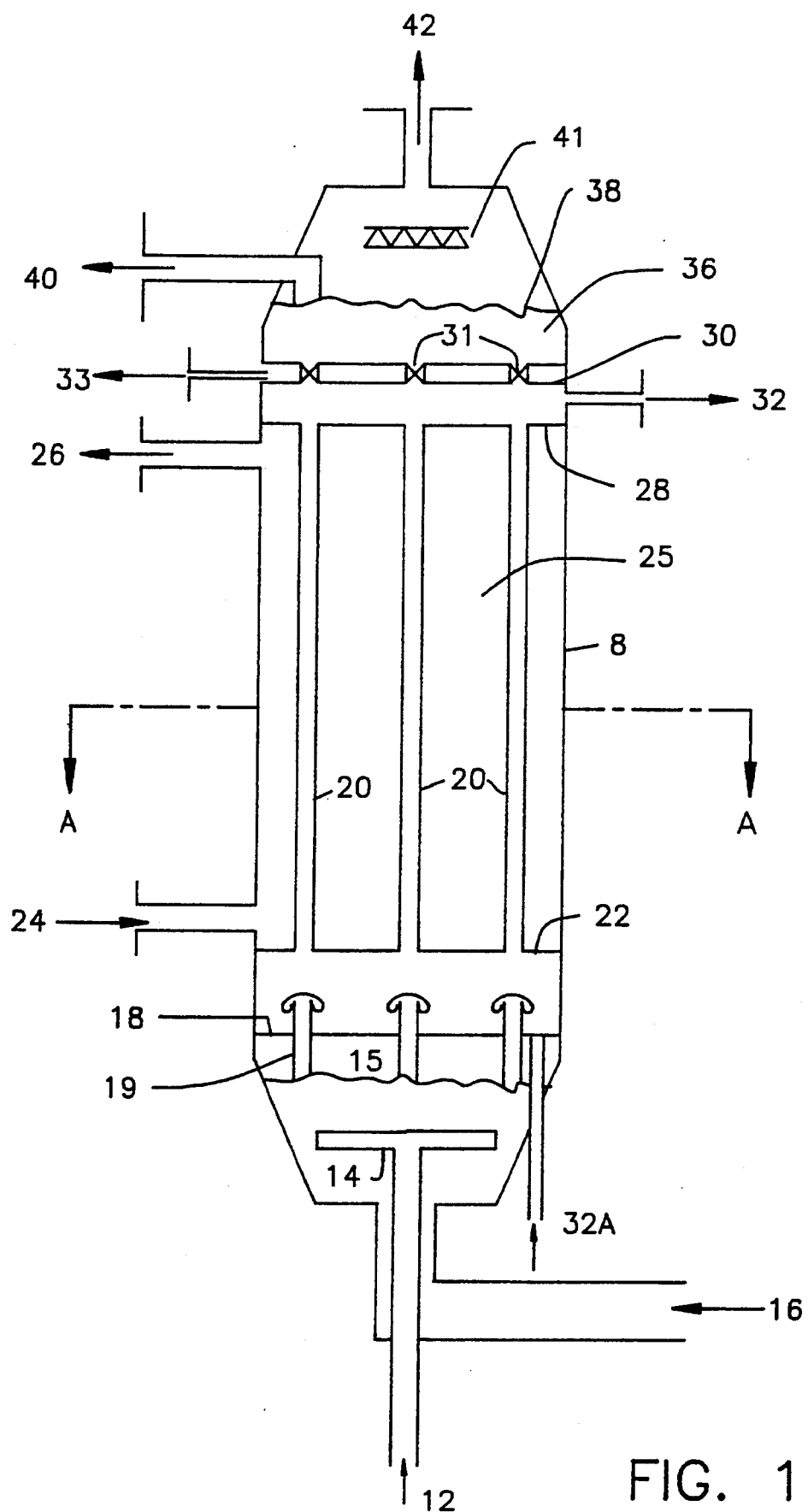
FIG. 1 is an elevation of a shell and tube reactor arrangement showing the gas, liquid, catalyst interconnection both above and below the upper and lower tube sheets.

Above the distributor tray 18 and below tube sheet 22 is a liquid zone allowing interconnection or communication between reaction zones, that may or may not contain catalyst particles. This liquid zone allows uniform mixing of gas and liquid and catalyst and allows even distribution of the liquid, gas and catalyst into the reaction zones. Slurry removal/addition can be made via conduit 32A into the space above distributor tray 18 and below tube sheet 22. The proximity of the tubes 20 to the bubble caps 19 is close enough to allow the process stream (gas, liquid, and catalyst) to move into the tubes but far enough to allow the slurry to move from tube to tube and provide a balance for slurry in each reaction zone. Such a zone may be readily designed by chemical engineers.

There are arranged in the housing 8 a multiplicity of essentially parallel, elongated reaction zones, e.g., tubes 20, which are vertically aligned, that is, aligned along the same longitudinal axis, with the slotted tubes and bubble caps 19. The energy supplied by the injected synthesis gas forces the gas up into the tubes 20 where the gas maintains the catalyst dispersed in the slurry liquid. Reaction takes place wherever there is catalyst and suitable reaction conditions, which include pressures ranging from 1 to 100 atmospheres, preferably 10 to 50 atmospheres, more preferably about 15 to 40 atmospheres and temperatures ranging from about 175° C. to about 400° C., preferably about 180° C. to 280° C., more preferably about 180° C. to 240° C.

Liquid recycle, for mixing purposes or for supplying additional energy for maintaining the catalyst dispersed is not essential, but may be supplied if desirable through line 16.

The slurry phase liquids in which the catalyst is dispersed are those that are liquid at reaction conditions, generally inert, and a good solvent for synthesis gas. Typically, the slurry is the product of the reaction and contains $C_5+$ hydrocarbons, usually $C_5$-$C_{50}$ hydrocarbons. Preferably, however, the slurry liquid comprises primarily high boiling paraffins with small amounts of primary and secondary alcohols, acids, esters, or mixtures thereof. Sulfur, nitrogen, phosphores, arsenic, or antimony heteroatoms are to be avoided since these tend to poison the hydrocarbon synthesis catalyst. Examples of specific slurry liquids are dodecane, tetradecane, hexadecane, octadecane, tetracosane, and the like. Preferred slurry materials are Fischer-Tropsch waxes and $C_{16}$-$C_{18}$ hydrocarbons.

The concentration of solids, including catalyst, in the slurry phase is usually about 10–50% by weight, preferably 30–40 wt % solids.

The hydrocarbon synthesis reaction is highly exothermic and the heat of reaction is removed by a heat transfer material 25 on the shell side of the shell and tube arrangement. The common heat transfer material can be any material having a high heat capacity, whether or not undergoing a phase change. Preferably, the heat transfer fluid is boiling water, and shell side cooling water enters the housing 8 through inlet 24 and exits either as boiling water or as steam through outlet 26. The heat transfer fluid is free to contact the external surfaces of all or substantially all of the reaction zones. The heat transfer fluid, however, is not in fluid communication with the slurry phase. That is, for example when water is the heat transfer fluid, it does not mix with the hydrocarbon slurry liquid or hydrocarbon product or synthesis gas feed. The water flows through a system completely separate from the process system containing feed, slurry, and products.

The upper portions of the tubes 20 are secured in an upper tube sheet 28, the length of the tubes or reaction zones being sufficient to provide an L/D ratio of at least about 10, preferably at least about 20, and most preferably at least about 40.

There is a liquid space above the upper tube sheet and from which catalyst slurry addition or removal may be made through line 32. This liquid space allows interconnection or communication between the upper ends of reaction zones for gas, liquid, and catalyst. Above the liquid space is another tube sheet 30 holding filter cartridges 31 which may contain sintered metal mesh, woven metal fibers, glass fibers, cloth, fibrous carbon that can remove the catalyst particles while allowing passage of the liquid. The filter cartridges are each vertically aligned with each reaction zone and prevent catalyst particles from reaching the upper portion of the housing 8. Above the filter cartridge tube sheet is a gas-liquid disengagement zone 36 topped by a foamy interface 38. Liquid product from the hydrocarbon synthesis may be removed via line 40, or alternately via line 33 at or above the filter cartridge tube sheet. A demistor 41 finally separates gas from liquid droplets and residue gases are withdrawn via line 42. Thus, the liquid space above the upper tube ends and below the filter tube sheet allows fluid communication between the upper tube ends and the alternate slurry addition/-removal conduit 32 as well as the space above the filter tube sheet. The space above the filters and filter tube sheet allows fluid communication of the gas outlet means, the liquid outlet means and the space below the filter tube sheet, thereby further allowing fluid communication to the upper ends of the reaction tubes.

Figure 2:
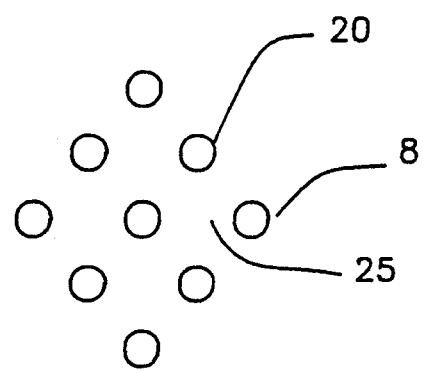
FIG. 2 shows a horizontal section A—A through the elevation of FIG. 1 showing a possible arrangement of tubes, that is, reaction zones.

FIG. 2 is a horizontal section through about the center of the housing and shows the reactions zones 20 arranged in the housing 8 and surrounded by a common heat transfer medium 25.

Figure 3:
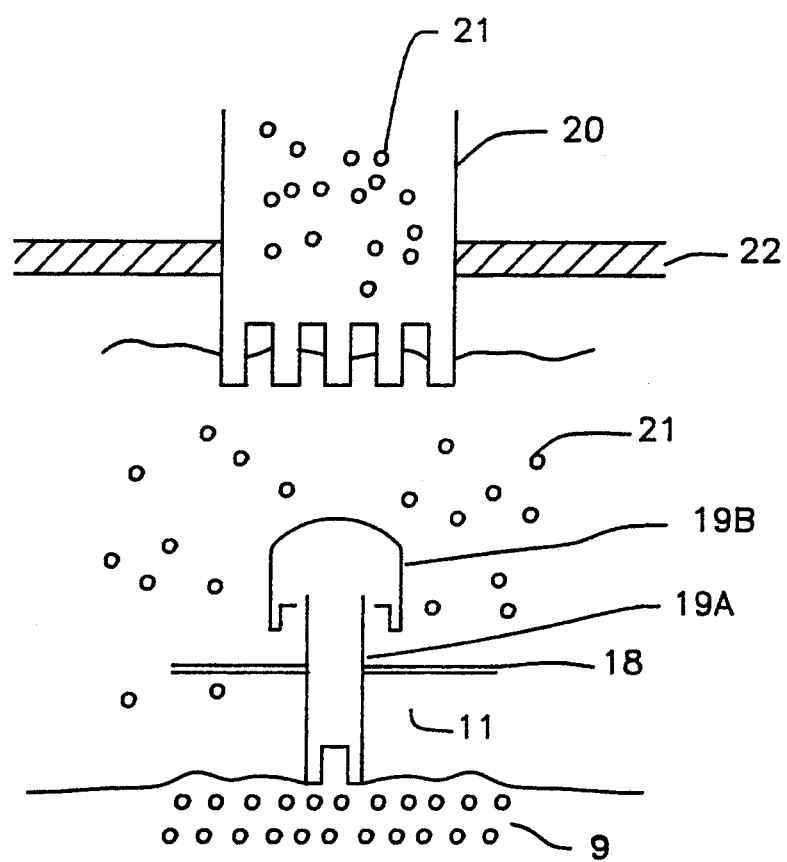
FIG. 3 is a detail of a possible distribution zone for one reaction tube/zone.

FIG. 3 is a proposed detail of the distribution zone for a reaction zone/tube. By virtue of energy supplied by the synthesis gas feed, sparged, bubbly liquid in area 9 enters the slotted bubble cap tube, where the tube is 19A and the bubble cap is 19B. The area above and outside the slotted tube 19A entry is a vapor space 11. The bubble cap/tube 19 is aligned vertically with the tube/reaction zone 20. The bubble cap 19B is operatively connected to the tube 19A which is about ½-3 inches diameter, the bubble cap is sized to give a pressure drop and injection velocity sufficient to decrease the size of the bubbles and suspend catalyst particles 21 in that reaction zone. In particular, the bubble cap is about ½ to 4-½ inches in diameter and the injection velocity at this point is about 20 to 100 ft/sec.

Thus, not only is bubble size decreased vis-a-vis bubbles coming out of the sparget but an agitated flow is also created. The flow is sufficient to lift and disperse catalyst particles 21, that are in the liquid zone above the distributor 18 and the lower tube sheet 22, into the reaction zone/tube 20. The arrangement and sizing of the bubble caps allow for relatively small, substantially uniform bubbles such that gas/liquid mass transfer rates are enhanced, thereby enhancing catalyst life and CO conversion. The gas to liquid mass transfer rates are at least about to the conversion rate of synthesis gas with minimal loss in reactions driving free due to mass transfer resistances. Minimizing such resistances reduces total pressure requirements and achieves high productivity. Lower pressure also reduces equipment and operation expenses.

From the arrangement shown in the drawings, the slurried catalyst is preferably maintained within the reaction tubes although some catalyst may optionally be present in the liquid zones or plenum above and below the upper and lower tube sheets, leading to the interconnection (or communication between) of the reaction tubes for gas, liquid, and slurry.

During operation each reaction zone/tube operates essentially independently of the other reaction zones/tubes even though they are interconnected for all three phases. The rates of gas, liquid, and solid flows through each tube are metered by having a liquid space below the lower tube sheet and above the distributor tray allowing communication between tubes.

Catalyst dispersion in the reaction zones is maintained essentially by energy supplied by the injected and rising synthesis gas. Other means are known for providing energy catalyst dispersion, e.g., slurry recycle, liquid recycle, but it is preferred to provide the energy substantially from injected synthesis gas, i.e., at least 50% thereof, preferably at least 90%, more preferably at least 95% thereof.

The catalyst employed in the hydrocarbon synthesis process is any catalyst known to be active in Fischer-Tropsch synthesis. For example, Group VIII metals, whether supported or unsupported, are known Fischer-Tropsch catalysts. Of these, iron, cobalt and ruthenium are preferred, particularly iron and cobalt, most particularly cobalt.

A preferred catalyst is supported on an inorganic refractory oxide selected from Groups III, IV, V, VI, and VIII of the Periodic chart of the elements. Preferred supports include silica, alumina, silica-alumina, the Group IVB oxides, most preferably Group IVB oxides, specifically titania (primarily in the rutile form), and generally supports having a surface area of less than about 100 m$^2$/gm, preferably less than about 70 m$^2$/gm.

The catalytic metal is present in catalytically active amounts, usually about 1-50 wt %, preferably 2-40 wt %, more preferably about 2-25 wt %. Promoters may be added to the catalyst and are well known in the Fischer-Tropsch catalyst art. Promoters can include ruthenium (when it is not the primary catalytic metal), rhenium, hafnium, cerium, and zirconium, and are usually present in amounts less than the primary catalytic metal (except for ruthenium which may be present in co-equal amounts), but the promoter:metal ratio should be at least about 1:10. Preferred promoters are rhenium and hafnium.

Catalyst preparation can be any of a variety of methods including impregnation, spraying and particularly the method described in U.S. Pat. No. 4,621,072 incorporated herein by reference.

Catalyst particle size is not critical and particle sizes may range from that which is reasonably filterable to that which can be reasonably dispersed in a slurry phase. Particles sizes of 1-200 microns, preferably about 20-150 microns meet these requirements.

Example

A bubble column reactor consisting of a 6 inch, Schedule 80 stainless steel pipe about 50 feet in length was mounted inside a 12 inch pipe that served as the cooling jacket. The internal diameter of the reactor was 5.76 inches. Feed gas to the reactor was preheated and injected through a single, ½ inch nozzle at the bottom of a conical inlet section. The height of the gas-liquid-solid slurry varied from about 12 feet to about 32 feet. An axial thermocouple rake provided a definition of the reactor temperature profile. A gas jet, installed just above the normal liquid level of the slurry, controlled foam formation and allowed exit gas velocities up to 7.9 cm/sec to be used.

The cobalt containing catalyst was prepared by impregnation of titania extrudates, which were then crushed and screened to provide the desired particle size of about 30 microns mean diameter. The catalyst was activated in the reactor, before a slurry wax liquid was introduced, by passing hydrogen upflow through the fluidized solids.

Starting at a low feed ratio of 1.7 $H_2$/CO and a gas superficial velocity of 3.5 cm/s (about 2200 GHSV), the unit lined out quickly, achieving a steady CO conversion level in excess of 50% (then at a 2800 GHSV) within four hours. After a slight drop in conversion to about 45% in the first 14 hours, the feed ratio was increased to 2.1 (at constant feedrate) to prevent any $H_2$ depletion-related deactivation that might have been occurring. The unit responded with a dramatic increase in conversion, up to about 58%, quickly lining out at about 54%.

Following a unit upset (overhead carryover induced by increasing feedrates) and a brief shutdown, the unit was restarted, this time at a higher gas feedrate (5 cm/sec), a higher steam jacket pressure (140 psig), and a higher reactor pressure (285 psig at the reactor gas outlet). Conversion promptly reached 58%, then continued to increase to 65%+. The unit maintained extremely high conversion levels, in the range of 60% to 70%. Over the range of space velocities tested, from 2800 to 3600 (hr$^{-1}$), CO productivities ranged from 450 to 750 for this very active HCS catalyst. After nearly seven days on synthesis, there was no significant activity loss and methane selectivities were low (2.7% to 3.2%). Filtration of the hydrocarbon synthesis liquid (wax) was easy at flux rates in the range of 0.13 to 0.2 gpm/ft$^2$. After 120+ hours on the first post-blowback cycle, the 0.175 ft$^2$, 18 micron, Regimesh ® filter showed no indication of needing a second backflush.

What is claimed is:

1. A hydrocarbon synthesis process comprising reacting a gaseous mixture of hydrogen and carbon monoxide at a pressure of 1 to 100 atmospheres and a temperature of about 175° C. to about 400° C. in the presence of a hydrocarbon synthesis catalyst dispersed in a liquid thereby forming a slurry liquid, wherein the catalyst dispersion is disposed in a plurality of vertically arranged elongated reaction tubes having an L/D (length/diameter) of at least about 10, each tube being surrounded by a common heat transfer medium disposed within the shell of a shell and tube reactor, the heat transfer medium not being in fluid communication with the slurry liquid.

2. The process of claim 1 wherein the energy for maintaining the catalyst dispersed in the reaction zone is supplied essentially completely by injection of the gaseous mixture.

3. The process of claim 1 wherein substantially all of the catalyst is maintained in the reaction zones.

4. The process of claim 1 wherein the catalyst is a Group VIII metal containing catalyst.

5. The process of claim 4 wherein the catalyst is a cobalt containing catalyst.

6. The process of claim 5 wherein the cobalt catalyst is supported.

7. The process of claim 5 wherein the gaseous mixture is injected into an essentially catalyst-free liquid, the energy of the gaseous mixture being sufficient to carry the liquid to the reaction zone.

* * * * *